(12) United States Patent
Schneider et al.

(10) Patent No.: US 11,648,049 B2
(45) Date of Patent: May 16, 2023

(54) DEVICES AND METHODS WITH MONOPOLAR AND BIPOLAR FUNCTIONALITY

(71) Applicant: Cilag GmbH International, Zug (CH)

(72) Inventors: Matthew Schneider, Blue Ash, OH (US); Mark Glassett, Madisonville, LA (US); Richard Timm, Cincinnati, OH (US); Chad Frampton, American Fork, UT (US); Monica Rivard, Cincinnati, OH (US); Drew Whitney, Cincinnati, OH (US); Ryan Asher, Cincinnati, OH (US); Paul Borgmeier, Cincinnati, OH (US); Darcy Greep, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 322 days.

(21) Appl. No.: 16/375,534

(22) Filed: Apr. 4, 2019

(65) Prior Publication Data
US 2020/0315692 A1   Oct. 8, 2020

(51) Int. Cl.
*A61B 18/14* (2006.01)
*A61B 18/12* (2006.01)
(Continued)

(52) U.S. Cl.
CPC ...... *A61B 18/1445* (2013.01); *A61B 18/1206* (2013.01); *A61B 17/2909* (2013.01); *A61B 2018/0063* (2013.01); *A61B 2018/00071* (2013.01); *A61B 2018/00196* (2013.01); *A61B 2018/00577* (2013.01); *A61B 2018/00589* (2013.01); *A61B 2018/00601* (2013.01); *A61B 2018/00607* (2013.01);
(Continued)

(58) Field of Classification Search
CPC ...... A61B 18/1445; A61B 2018/00071; A61B 2018/00589; A61B 2018/00601; A61B 2018/0063; A61B 2018/1226; A61B 2018/1253; A61B 2018/126
See application file for complete search history.

(56) References Cited

U.S. PATENT DOCUMENTS 6,299,625 B1 * 10/2001 Bacher ............... A61B 17/2909
606/205
9,820,806 B2 * 11/2017 Lee .................... A61B 18/1445
(Continued)

*Primary Examiner* — Joanne M Rodden
*Assistant Examiner* — Sean W Collins
(74) *Attorney, Agent, or Firm* — Mintz Levin Cohn Ferris Glovsky and Popeo, P.C.

(57) ABSTRACT

Surgical devices, systems, and methods are provided for applying monopolar energy and bipolar energy to tissue. In one embodiment, a surgical device is provided with an end effector that has first and second jaws movable between an open position and a closed position, and a conductive member that extends through the end effector. The conductive member has a retracted position in which the conductive member is substantially disposed within the end effector and an extended position in which the conductive member extends at least partially distally beyond the end effector. The conductive member is configured to conduct energy through tissue adjacent thereto when the conductive member is in the extended position. A trigger coupled to the handle is pivotally movable to move the conductive member between the retracted and extended positions.

16 Claims, 10 Drawing Sheets

(51) Int. Cl.
  *A61B 18/00* (2006.01)
  *A61B 17/29* (2006.01)
(52) U.S. Cl.
  CPC . *A61B 2018/126* (2013.01); *A61B 2018/1226* (2013.01); *A61B 2018/1253* (2013.01); *A61B 2018/1422* (2013.01); *A61B 2018/1467* (2013.01); *A61B 2018/1475* (2013.01)

(56) References Cited

U.S. PATENT DOCUMENTS

| | | |
|---|---|---|
| 10,010,309 B2 | 7/2018 | Bingham |
| 10,010,366 B2 | 7/2018 | Strobl |
| 2009/0202387 A1 | 8/2009 | Dlugos, Jr. et al. |
| 2011/0054469 A1* | 3/2011 | Kappus ............ A61B 18/1445 606/46 |
| 2011/0264093 A1* | 10/2011 | Schall ............... A61B 18/1445 606/52 |
| 2014/0005666 A1* | 1/2014 | Moua ................ A61B 18/1206 606/45 |
| 2014/0005682 A1* | 1/2014 | Worrell ................ A61B 34/76 606/130 |
| 2015/0066009 A1* | 3/2015 | Garrison ........... A61B 18/1206 606/34 |
| 2017/0135712 A1 | 5/2017 | Boudreaux |
| 2018/0280075 A1* | 10/2018 | Nott .................. A61B 18/1445 |

* cited by examiner

DEVICES AND METHODS WITH MONOPOLAR AND BIPOLAR FUNCTIONALITY

FIELD

Surgical devices, systems, and methods are provided for selectively applying monopolar energy and bipolar energy to tissue.

BACKGROUND

Various surgical devices can be used for minimally-invasive surgery to compress, transect, and seal different types of tissue. In general, these devices can have an end effector with a pair of opposed jaws that are configured to engage tissue therebetween and a cutting mechanism that is configured to transect tissue engaged by the opposed jaws. The end effectors can also be configured to apply electrical energy to tissue engaged between the opposed jaws. The application of electrical energy to the engaged tissue can seal and coagulate the tissue, such as to seal tissue being cut by the cutting mechanism to prevent or reduce bleeding.

However, various situations can arise during an operation in which a user wants to apply energy to tissue without having to first grasp tissue between the opposed jaws, such as to selectively apply energy to spots of tissue in a controlled manner without having to clamp and seal an entire section of tissue.

Accordingly, there remains a need for improved energy delivery methods and devices for treating tissue.

SUMMARY

Methods, devices, and systems are provided herein for selectively applying monopolar energy to tissue adjacent to a surgical instrument and bipolar energy to tissue grasped by the surgical instrument during minimally-invasive surgery.

In one aspect, a surgical device is provided that includes a handle with an elongate shaft extending distally therefrom. An end effector is operatively connected to a distal end of the elongate shaft, and the end effector has first and second jaws that are movable between an open position in which the first and second jaws are spaced apart from one another and a closed position in which the first and second jaws cooperate to grasp tissue therebetween. The first and second jaws are also configured to conduct energy through tissue grasped therebetween. A conductive member extends longitudinally through the first jaw, and the conductive member has a retracted position in which the conductive member is substantially disposed within the first jaw and an extended position in which the conductive member extends at least partially distally beyond a distal end of the first jaw. The conductive member is also configured to conduct energy through tissue adjacent thereto. The device further includes a trigger coupled to the handle and movable between an open position and a closed position. The trigger is pivotally movable through a first range of motion between the open position toward the closed position to cause the opposed jaws of the end effector to move from the open position to the closed position while the conductive member remains in the retracted position, and the trigger is pivotally movable through a second range of motion during which the jaws remain in the closed position and the conductive member moves from the retracted position to the extended position.

The surgical device can have numerous variations. For example, the conductive member can have a hook on the distal end thereof. The hook can be positioned distal of a distal end of the first jaw and can be oriented away from the second jaw. In other embodiments, energy can be supplied to the conductive member only in the extended position. In another aspect, energy can only be supplied to the first and second jaws when the conductive member is in the retracted position.

The first and second jaws can also be configured to transect tissue grasped therebetween. In one example, the surgical device can include a generator in the handle to supply energy to the first and second jaws and the conductive member. In another example, the surgical device can have an external plug extending proximally from the handle to supply energy to the first and second jaws and the conductive member.

In another aspect, a surgical device is provided that includes a handle with an elongate shaft extending distally therefrom. An end effector is operatively connected to a distal end of the elongate shaft, and the end effector has first and second jaws that are configured to grasp tissue therebetween and conduct energy through the grasped tissue therebetween. A closure grip extends from the handle and is pivotable relative to the handle to open and close the first and second jaws. A conductive member is selectively extendable distally from the end effector, and it is configured to conduct energy to tissue adjacent to the end effector. The surgical device has a bipolar mode in which the first and second jaws conduct energy through the grasped tissue therebetween and the conductive member is retracted proximally in the end effector. It also has a monopolar mode in which the conductive member is extended distally from the end effector and energy can only be conducted through the conductive member. The surgical device can transition between the bipolar mode and the monopolar mode in response to pivotable movement of the closure grip.

The surgical device can have any number of variations. For example, energy can be conducted through the conductive member only in the monopolar mode. In another example, the conductive member can have a hook on a distal end thereof. The hook can be positioned distal of a distal end of the first jaw and can be oriented away from the second jaw in the monopolar mode. In other embodiments, the first and second jaws also can be configured to transect tissue grasped therebetween.

In another aspect, a surgical method is provided that includes actuating a trigger assembly on a surgical device to pivotally move through a first range of motion to cause opposed first and second jaws of an end effector on the surgical device to move from an open position to a closed position. The method also includes actuating the trigger assembly to pivotally move through a second range of motion during which the first and second jaws remain in the closed position and a conductive member is distally advanced from the end effector to protrude distally beyond the end effector. The method further includes actuating an energy assembly to supply energy to the conductive member to treat tissue located adjacent thereto.

The surgical method can have various embodiments. For example, the method can include, after actuating the energy assembly, actuating the trigger assembly to pivotally move through the second range of motion such that the conductive member retracts proximally into the end effector. In another embodiment, the surgical method can include actuating the trigger assembly to pivotally move through the first range of motion to cause the first and second jaws to move to the closed position and grasp tissue therebetween. The method can further include actuating the energy assembly to supply energy to the first and second jaws to seal tissue grasped therein. In another example, the surgical method can include actuating a cutting assembly on the surgical device to transect tissue grasped between the first and second jaws.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
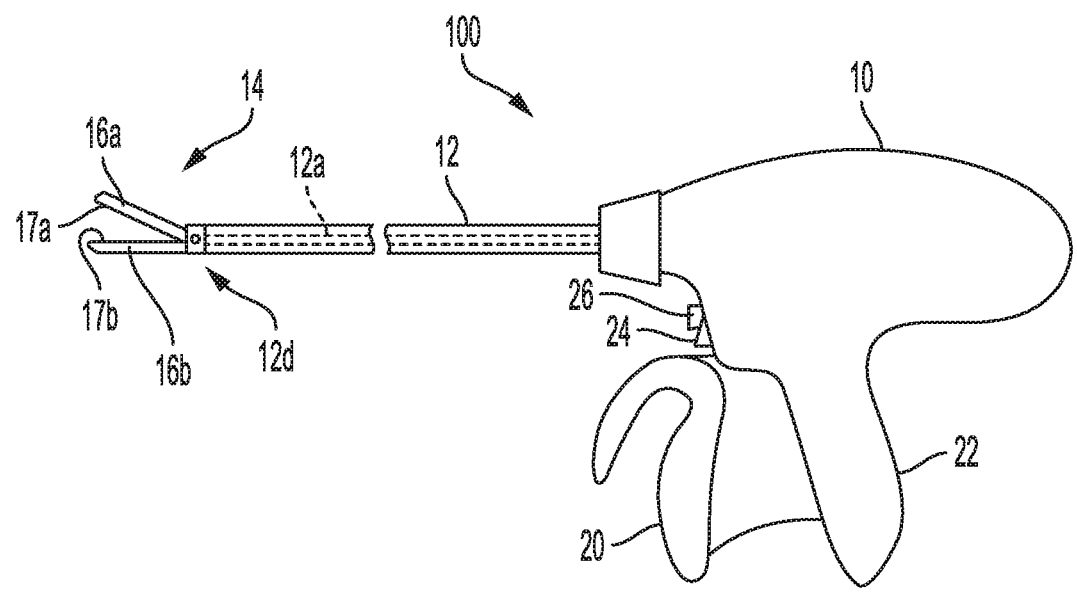
FIG. 1 is a side view of one embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, devices, and systems are provided for applying monopolar energy and bipolar energy to tissue from a surgical instrument, such as a minimally-invasive surgical instrument with an end effector that has opposed jaws for grasping tissue, transecting grasped tissue, and sealing grasped tissue. While tissue sealing can be accomplished by applying energy between the opposed jaws to grasped tissue, it can be beneficial to apply spot energy to target tissue that is adjacent to the end effector and not grasped thereby. This can allow a user to conduct spot coagulation, non-clamping sealing and/or hemostasis, marking tissue, cutting or searing tissue, etc., during use. The energy being applied to tissue grasped between the opposed jaws is often bipolar energy applied by an energy delivering electrode in one jaw and received by a return electrode in the opposed jaw, while applying spot energy to tissue adjacent thereto is preferably performed by a monopolar electrode to simplify the energy application process. As such, various mechanisms are provided for advancing and retracting a monopolar electrode for applying spot energy to target tissue using a closure handle that is also used to open and close the opposed jaws. When advanced, at least part of the monopolar electrode can protrude from the end effector to deliver energy to tissue adjacent thereto, and when retracted, the monopolar electrode can be at least partially withdrawn into the end effector such that at least a portion of the electrode is protected by the end effector.

In an exemplary embodiment, a surgical device is provided having a handle with an elongate shaft extending distally therefrom. An end effector can be operatively connected to a distal end of the elongate shaft, and the end effector can have first and second jaws. The first and second jaws can be movable between an open position in which the first and second jaws are spaced apart from one another and a closed position in which the first and second jaws cooperate to grasp tissue therebetween. In the closed position, the first and second jaws can conduct energy through tissue grasped therebetween. A conductive member can extend longitudinally through the first jaw, and the conductive member can have a retracted position and an extended position. In the retracted position, the conductive member can be substantially disposed within the first jaw, and in the extended position a distal end of the conductive member can be positioned distally to a distal end of the first jaw. The conductive member can be configured to conduct energy through tissue adjacent thereto. The device can also include a trigger assembly coupled to the handle and movable between an open position and a closed position. The trigger can be pivotally movable to cause the opposed jaws of the end effector to move between the open position and closed position, and it can be pivotally movable to cause the conductive member to move from the retracted position to the extended position for energy delivery.

FIG. 1 illustrates one embodiment of a surgical device configured to grasp and cut tissue. As shown, the illustrated surgical device 100 generally includes a proximal handle portion 10, a shaft portion 12, and an end effector 14 for grasping tissue. The proximal handle portion 10 can be any type of pistol-grip, scissor grip, pencil-grip, or other type of handle known in the art that is configured to carry various actuators, such as actuator levers, knobs, triggers, or sliders, for actuating various functions such as rotating, articulating, approximating, and/or firing the end effector 14. In the illustrated embodiment, the proximal handle portion 10 includes a stationary grip 22 and a closure grip 20 that is movable relative to the stationary grip 22 to open and close jaws of the end effector 14. The shaft portion 12 extends distally from the proximal handle portion and has at least one lumen 12a extending therethrough for carrying mechanisms for actuating the end effector 14. The end effector 14 can have a variety of sizes, shapes, and configurations. As shown in FIG. 1, the end effector 14 includes a first upper jaw 16a and a second lower jaw 16b disposed at a distal end 12d of the shaft portion 12. The jaws 16a, 16b are moveable between an open position in which the jaws 16a, 16b are spaced a distance apart, as shown in FIG. 1, and a closed position in which the jaws 16a, 16b are moved toward one another and are substantially opposed. When the jaws 16a, 16b are in the closed position, a longitudinal axis of the upper jaw 16a can be substantially parallel to a longitudinal axis of the lower jaw 16b and the jaws 16a, 16b can act to engage or grasp tissue therebetween. In the illustrated embodiment, the upper jaw 16a pivots relative to the shaft portion 12 and relative to the lower jaw 16b while the lower jaw 16b remains stationary, however in other embodiments both jaws can pivot. While the illustrated jaws 16a, 16b have a substantially elongate and straight shape, a person skilled in the art will appreciate that one or both of the jaws 16a, 16b can curve in various directions, such as being curved along a longitudinal length thereof. The jaws 16a, 16b can have any suitable axial length for engaging tissue, and the length can be selected based on the targeted anatomical structure for transection and/or sealing.

As indicated above, the surgical device 100 can have a closure actuator that can be configured to open and close the jaws 16a, 16b of the end effector 14 such that the jaws can engage tissue, move anatomical structures, or perform other surgical functions. While the closure actuator can have various configurations, as indicated above the closure actuator includes the closure grip 20 and the stationary grip 22. The closure grip 20 can be pivotable toward and away from the stationary grip 22. In particular, the closure grip 20 can have a first or initial open position in which it is angularly offset and spaced apart from the stationary grip 22 and the jaws 16a, 16b of the end effector 14 are open. It can also have a second or final closed position where it is positioned adjacent to, or substantially in contact with, the stationary grip 22 and the jaws 16a, 16b of the end effector 14 are substantially closed to engage tissue and apply a force to tissue disposed therebetween. The closure grip 20 can be biased to the first open position with the jaws 16a, 16b of the end effector 14 being open, as shown in FIG. 1.

The closure grip 20 can use manual or powered components. For example, in manually actuated embodiments, the closure grip 20 can be coupled to one or more gear(s), rack(s), drive screw(s), drive nut(s), etc. disposed within the handle. In powered embodiments, a motor can be disposed in the proximal handle portion 10 and manual movement of the closure grip 20 can cause a control signal to be sent to the motor, which can interact with various gears or other components to cause the jaws 16a, 16b to close. The closure grip 20 can also interact with one or more locking features to lock the closure grip 20 relative to the stationary handle 22. For example, the locking feature can automatically engage when the closure grip 20 substantially contacts the stationary handle 22 or the locking feature can automatically engage at each position the closure grip 20 is pivoted through, such as via ratcheting.

Figure 2:
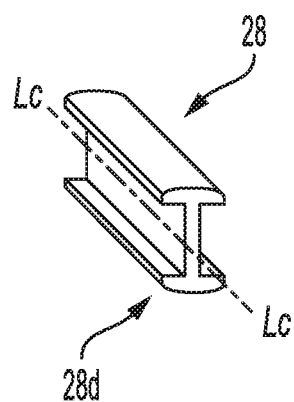
FIG. 2 is a perspective view of a compression member of the surgical device of FIG. 1.
Figure 3:
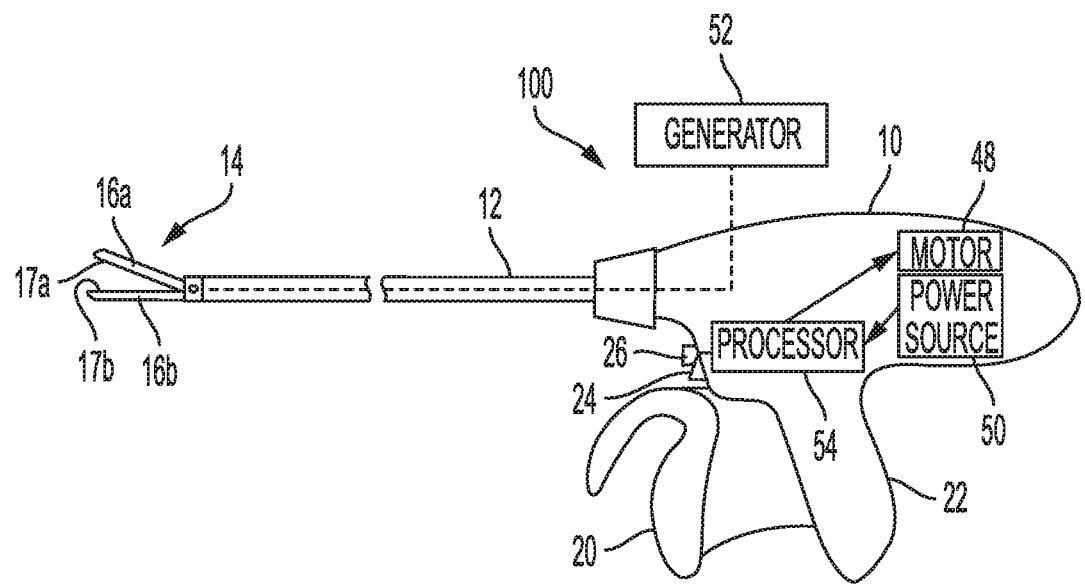
FIG. 3 is another side view of the surgical device of FIG. 1.

The surgical device 100 can also have one or more additional activators that can be separate from the closure actuator 20, such as a cutting actuator 24 to advance a cutting assembly and a sealing actuator 26 to apply energy to tissue. While the actuators 24, 26 can have various configurations, the illustrated actuators 24, 26 are buttons or triggers that can be depressed by a user and can activate various elements in the device to advance the cutting element and/or cause energy to be delivered to the jaws. For example, the cutting actuator 24 can be in manual or electrical communication with various gear(s), rack(s), drive screw(s), drive nut(s), motor(s), and/or processor(s). The cutting assembly can be configured to transect tissue captured between the jaws, and it can be sized and shaped to transect or cut various thicknesses and types of tissue. In one exemplary embodiment, as shown in FIG. 2, the cutting assembly can include an I-beam compression member 28 that travels along a longitudinal axis Lc through slots formed in each jaw to pull the jaws into a parallel orientation, to compress tissue therebetween, and to transect tissue using a cutting element on the distal end 28d thereof. As shown in FIG. 3, the handle portion 10 of the surgical device 100 can include other components for operating the device, such as a motor 48, a power source 50, a generator 52, and/or a processor 54, as well as various sensors (not shown).

The device 100 can also include various components for delivering energy, such as radiofrequency (RF) or ultrasound energy, to tissue, and these components can be disposed at various locations in the device 100, such as in the proximal handle portion 10 and/or in one or both of the jaws 16a, 16b. The sealing actuator 26 can be coupled to the processor 54, and the processor 54 can be coupled to the motor 58, the power source 50, and/or the generator 52 (as well as any sensors provided). Depressing the actuator 26 can send a signal to the processor 54, which can cause delivery of energy from the generator 52 and/or the power source 50 to tissue engaged by or adjacent to the end effector 14. The generator 52 can be incorporated into the handle portion 10 or can be a separate unit that is electrically connected to the surgical device 100. The generator can be any suitable generator known in the art, such as an RF generator or an ultrasound generator. The lumen 12a of the shaft portion 12 can carry electrical leads, conductive members, wires, etc. that can deliver electrical energy to components of the end effector 14 upon depression of the actuator 26. Both the generator 52 and the power source 50 can be batterypowered, can include batteries therein, and/or can be coupled to an external power source, such as an electrical outlet.

Upon actuation of energy delivery, energy can be delivered to one or more electrodes in one or both of the jaws 16a, 16b for delivering electrical current to tissue grasped therebetween to effect sealing, marking, cutting, etc. of tissue. The illustrated device 100 is a bipolar jaw device such that one of the jaws 16a, 16b can include an active electrode 17a for energy delivery, and the opposed jaw 16a, 16b can include a return electrode 17b. The return electrode 17b is electrically isolated from the active electrode 17a such that energy can be applied to tissue grasped between the jaws 16a, 16b from the active electrode 17a and can have a return path through the return electrode 17b. However, monopolar jaw devices can also be provided in which one or both jaws 16a, 16b include only an active, energy delivering electrode, and an energy return path can be through surrounding tissue, through the device 100 generally, through a ground pad placed on a patient's body, etc. For further details regarding actuation and use of exemplary surgical devices similar to device 100, see U.S. Pat. No. 10,010,366, entitled "Surgical Devices And Methods For Tissue Cutting And Sealing," filed Dec. 17, 2014; U.S. Pat. No. 10,010,309, entitled "Surgical Device With Overload Mechanism," filed Oct. 10, 2014; and U.S. Patent Pub. No. 2017/0135712, entitled "Methods And Devices For Auto Return Of Articulated End Effectors," filed Nov. 17, 2015; each of which is incorporated by reference herein in its entirety.

Figures 5A, 5B:
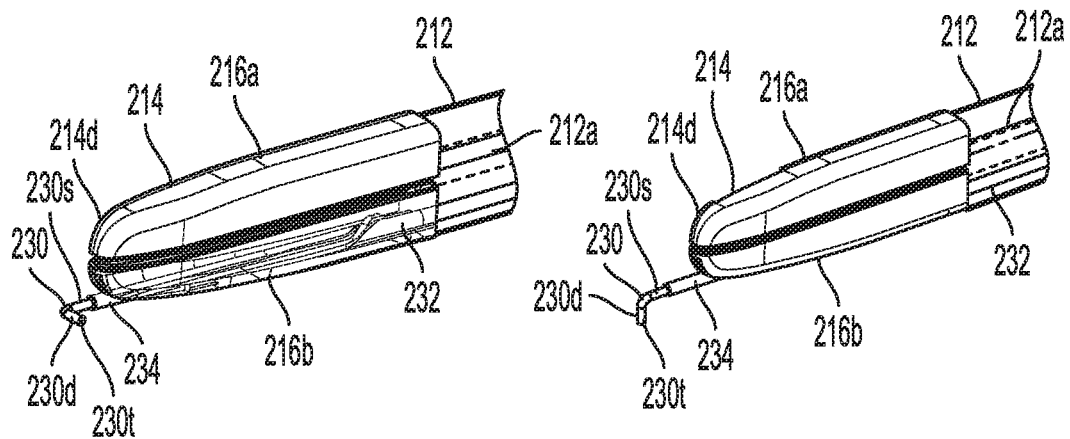
FIG. 5A is a partially-transparent perspective view of the end effector of FIG. 4A.
FIG. 5B is a perspective view of the end effector of FIG. 4A.
Figure 6:
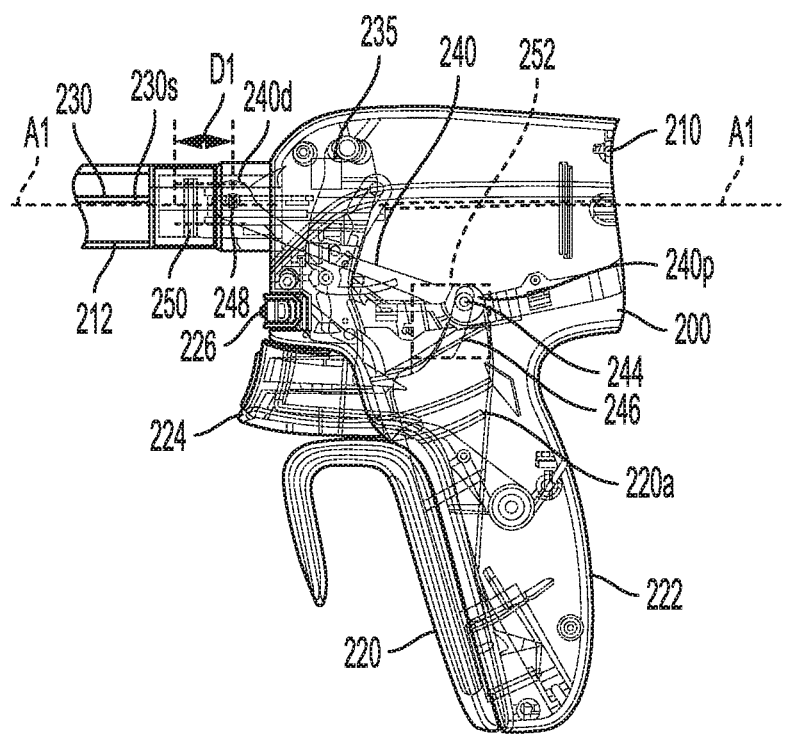
FIG. 6 is a partially-transparent side view of a proximal portion of the surgical device of FIG. 4A, showing a trigger in an actuated position.
Figure 7:
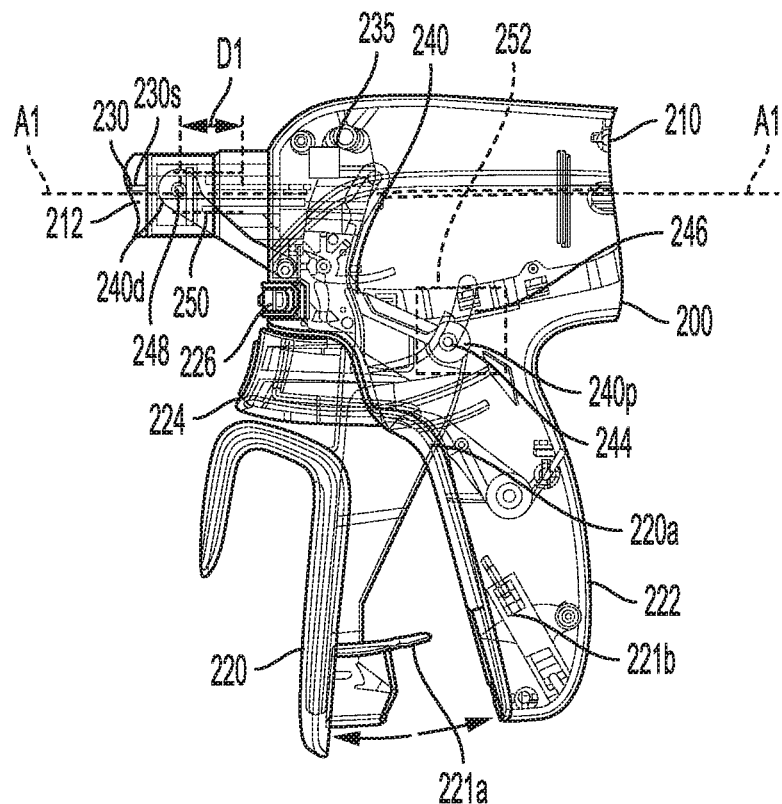
FIG. 7 is a partially-transparent side view of the surgical device of FIG. 4A, showing a trigger in an initial, unactuated position.

While energy can be delivered to tissue grasped between the opposed jaws 16a, 16b in the device 100, energy can also be delivered to tissue without having to grasp tissue by advancing one or more monopolar electrodes from the end effector. FIGS. 4A-7 illustrate an embodiment of a surgical device 200 similar to surgical device 100. All of the aforementioned features of device 100 are present on device 200. In particular, surgical device 200 has a proximal handle 210, an elongate shaft 212, and an end effector 214. The shaft 212 extends distally from the proximal handle 210 and has the end effector 214 disposed on a distal end thereof, and it has at least one lumen 212a extending therethrough for carrying mechanisms for actuating the end effector 214. The end effector 214 has a first upper jaw 216a and a second lower jaw 216b that is opposed thereto. The jaws 216a, 216b can grasp tissue therebetween, transect grasped tissue with a cutting element 218, and apply bipolar energy to grasped tissue through active and return electrodes 219a, 219b in the jaws 216a, 216b. The proximal handle 210 includes a stationary grip 222 and a closure grip 220 that is pivotally movable relative to the stationary grip 222, as illustrated by the arrows of FIG. 7, to open and close the jaws 216a, 216b of the end effector 214. The cutting actuator 224 is disposed on the proximal handle 210 to cause transection of tissue grasped by the jaws 216a, 216b, and the energy actuator 226 is disposed on the proximal handle 210 to cause delivery of energy to the end effector 214. Various gear(s), rack(s), drive screw(s), drive nut(s), motor(s), processor(s), conducting member(s), etc. can be disposed within the proximal handle 210 and the shaft 212 to translate actuation of the closure grip 220 and the actuators 224, 226 into actuation of functions on the end effector 214.

Figure 4A:
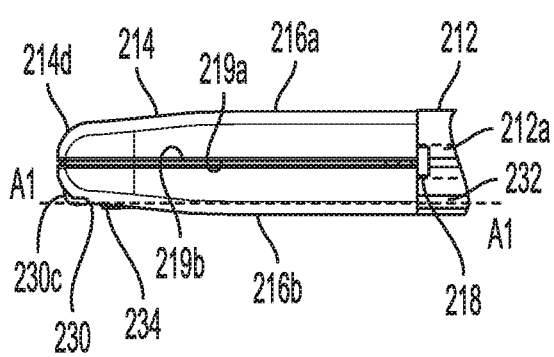
FIG. 4A is a side view of an end effector on another embodiment of a surgical device.
Figure 4B:
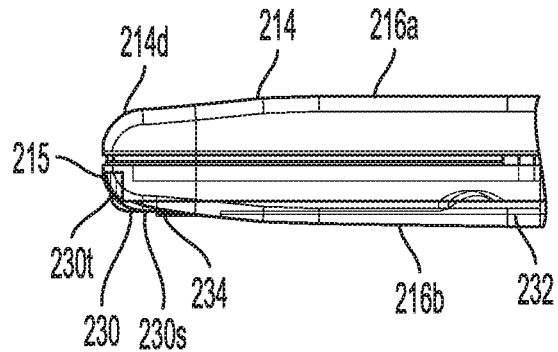
FIG. 4B is a partially-transparent side view of the end effector of FIG. 4A.

A monopolar electrode 230 extends longitudinally through at least a portion of the end effector 214 and is longitudinally translatable distally and proximally with respect thereto. The electrode 230 can translate between a retracted position in which a majority of the electrode 230 is retracted within the end effector 214, as illustrated in FIGS. 4A and 4B, and an extended position in which at least a distal end 230d of the electrode 230 protrudes distally beyond a distal end of the end effector 214, as illustrated in FIGS. 5A and 5B. Upon distal translation of the electrode 230 and actuation of energy, as discussed below, the electrode 230 can be used to spot seal, coagulate, mark, cut, etc. tissue disposed adjacent to the distal end 214d of the end effector 214. While the electrode 230 in the illustrated extends through the end effector and the shaft 212, it can extend parallel to but outside of one or both of the end effector 214 and the shaft 212 in other embodiments.

While the configuration can vary, in the illustrated embodiment the electrode 230 has an L shape with an elongate rod 230s and a hook or bent tip 230t on a distal end thereof that extends at an approximately right angle thereto. The rod 230s extends proximally through a longitudinal lumen 232 that extends through the second jaw 216b to engage with one or more conductive members in the proximal handle 210 for receiving energy therefrom. In the retracted position, the hook 230t can be received in a channel 217 on a distal end of the second jaw 216b. As illustrated in FIGS. 4A and 4B, at least a portion, such as the corner 230c of the electrode 230, can still protrude from the lumen 232 and the channel 217 such that surrounding tissue can still be exposed to and spot treated by the electrode 230 even in the retracted position. As such, a user can perform minor tissue modifications, such as limited spot coagulation, without having to extend the electrode. However, a majority of the electrode 230 is received into the end effector 214, and energy can be selectively terminated to the electrode 230 so that no energy is delivered thereto. This avoids any accidental energy application during movement, treatment, etc. Furthermore, in other embodiments, the electrode can be withdrawn entirely into the end effector.

In the extended position, the rod 230s and the hook 230t can be rotatable about a longitudinal axis A1 of the shaft. The hook 230t has a set rotational movement during distal extension, such as protruding away from the upper jaw 216a and approximately parallel to the stationary grip 222 upon full distal extension, as illustrated during partial rotation and extension in FIG. 5A and full rotation and extension in FIG. 5B. However, in other embodiments, it can be selectively rotatable by a user through a rotational mechanism on the proximal handle 210, such as by using a rotational knob, dial, etc. The hook 230t can thus protrude radially outward in any of 360 degrees of rotation relative to the rod 230s in some embodiments.

The electrode 230 can also have a non-conductive protective sleeve 234 that seals a majority of the electrode as it passes through the device 200, while terminating proximal to the hook 230t. As such, the electrode 230 has an exposed, electrically-active distal portion. The sleeve 234 can thus help protect various components within the device 200 and any secondary tissue from inadvertent electrical exposure while creating an easily-identifiable active distal end on the electrode 230 for treatment of any target tissue. The electrode 230 can be made from a variety of electrically-conductive materials, such as metal.

Distal and proximal translation of the electrode can be controlled by pivotable movement of the closure grip 220 relative to the stationary grip 222. In a closed position in which the closure grip 220 is positioned adjacent to or substantially in contact with the stationary grip 222, as illustrated in FIG. 6, the jaws 216a, 216b are in the closed position and the electrode 230 is in the retracted position, as illustrated in FIGS. 4A and 4B. During movement of the closure grip 220 away from the stationary grip 222 to an open position, as illustrated in FIG. 7, the electrode 230 is translated distally so that it protrudes distally beyond the end effector 214 for monopolar treatment of target tissue, as illustrated in FIGS. 5A and 5B.

The closure grip 220 can move through a range of pivotable motion during opening and closing. As such, it pivotally moves between a fully open initial position in which the closure grip 220 is positioned as far away from the stationary grip 222 as possible (for example, representing one hundred percent open) and a final closed position in which the closure grip 220 is adjacent the stationary handle 222 (for example, representing zero percent open). FIG. 6 illustrates the closure grip 220 in the closed position in which it is adjacent to the stationary handle 222. Opening movement of the closure grip 220 away from the stationary grip 222 begins distal translation of the electrode 230. As the closure grip 220 approaches a certain point during pivotable movement away from the stationary grip, such as at approximately halfway or 50 percent open, as illustrated in FIG. 7, the electrode 230 can reach a fully-extended position, as illustrated in FIG. 5B. At this point in pivotable movement of the closure grip 220, the jaws 216a, 216b are still in the closed position, as illustrated in FIG. 5B. Further opening movement of the closure grip 220 (for example, between fifty percent open and 100 percent open) can cause the jaws 216a, 216b to move to the open position. Subsequent pivotable movement to close the closure grip 220 can cause corresponding closing and retracting movement of the jaws 216a, 216b and the electrode 230. For example, pivotable closing movement can cause closure of the jaws 216a, 216b as the closure grip 220 moves from one hundred percent open (e.g. fully open) to approximately fifty percent open without moving the electrode 230. As the closure grip 220 moves from approximately fifty percent to zero percent open (e.g. fully closed), it can cause retraction of the electrode 230 while the jaws 216a, 216b remain closed.

However, the order of jaw opening relative to electrode translation and the exact points of transition during opening and closing of the closure grip 220 can vary in other embodiments. For example, opening movement of the closure grip 220 away from the stationary grip 222 can begin transition of the jaws 216a, 216b from the closed position to the opened position. As the closure grip 220 approaches a certain point during pivotable movement, such as at approximately halfway or 50 percent open, the jaws 216a, 216b can reach the fully opened position while the electrode 230 remains stationary. At this point in pivotable movement of the closure grip 220, the electrode 230 is still in the retracted position. Further opening movement of the closure grip 220 (for example, between fifty percent open and one hundred percent open) can then cause the electrode 230 to move to the extended position. Similar to the previous embodiment, pivotable movement to close the closure grip in this embodiment can cause corresponding retraction and closing movement of the electrode 230 and the jaws 216a, 216b.

Thus, a neutral or resting position of the device in this embodiment is reached when the closure grip 220 is approximately fifty percent open, as the jaws 216a, 216b are open and the electrode 230 is retracted. As such, the closure grip 220 can be biased to the transition point between opening the jaws 216a, 216b and extending the electrode 230 at approximately fifty percent open. Because of this biasing point, the jaws 216a, 216b are biased open but the electrode 230 is effectively biased to the retracted position. To extend the electrode 230, the user applies a further opening force to the closure grip 220 to pivotally move the closure grip 220 to the fully opened position (e.g. one hundred percent open) to overcome the biasing force. Accidental extension of the electrode 230 can thus be avoided.

In other embodiments, the closure grip 220 can be biased to the fully opened position (e.g. at one hundred percent open), to the fully closed position (e.g. at zero percent open), or any point therebetween (e.g. the transition point between actuating the jaws and actuating the monopolar electrode). The biased position can thus be the resting or neutral position. Additionally, the exact transition point between opening the jaws and extending the electrode (e.g. the percentage open and/or the degree of pivotable movement by the closure grip 220) can vary.

One or more locking 221a, 221b and/or ratcheting features can also be incorporated to lock the closure grip 220 at varying degrees of pivotable movement relative to the stationary handle 222. For example, a locking feature can automatically engage when the closure grip 220 substantially contacts the stationary handle 222, at the transition point between opening/closing the jaws and extending/retracting the electrode, and/or at a plurality of positions through which the closure grip 220 is pivotally moved, such as via ratcheting. As such, a user may be required to release the locking feature to continue further pivotable movement of the closure grip 220.

Pivotable movement of the closure grip 220 is translated to proximal and distal movement of the electrode 230 through one or more linkages or camming mechanisms in the proximal handle 210. The closure grip 220 has an extension wing 220a that extends proximally into the proximal handle 210 and couples to a proximal end 240p of a first linkage 240 by a pin 244. The pin 244 is pivotable relative to the wing 220a and the first linkage 240 and is slidably disposed within a groove or channel 246 in the proximal handle 210. The first linkage 240 extends distally toward the shaft 212, and a distal end 240d of the first linkage 240 couples to an engagement member 248 positioned in a proximal end of the shaft 212. The engagement member 248 couples to a proximal end of the rod 230s of the electrode 230. It can thus pivot relative to the distal end 240d of the first linkage 240 and can translate proximally and distally to cause linear translation of the electrode 230 along a lumen or channel 250, remaining engaged thereto. The channel 250 can be a separate channel or it can be incorporated into either lumen 212a or lumen 232. Thus, upon pivotable movement of the closure grip 220 from the closed position, illustrated in FIG. 6, to the open position, illustrated in FIG. 7, the extension wing 220a of the closure grip 220 rotates distally upward, causing the pin 244 to translate along the channel 246 and the proximal end 240p of the first linkage 240 to translate distally through the proximal handle 210. Distal translation of the first linkage 240 advances the engagement member 248 distally along the channel 250, which causes the rod 230s of electrode 230 to translate distally along the channel 232. As illustrated in FIGS. 6 and 7, the engagement member 248 and the rod 230s of the electrode 230 are thus translated distally by a distance D1 upon opening of the closure grip 220 to result in full distal extension of the distal end 230d of the electrode 230. The engagement member 248 can remain in linear engagement with the rod 430s even upon rotation of the hook 230t from the retracted orientation in FIG. 4A to the extended orientation in FIG. 5B. While a single linkage is used in the illustrated embodiment, a plurality of linkages can be used to navigate through the proximal handle 210 without obstructing other internal components. Additionally, the rod 230s translates during select ranges of motion of the linkage 240 and/or the closure grip 220 due to a cam mechanism 252, however in some embodiment, the proximal handle 210 can incorporate various biasing mechanisms, cam mechanisms, linkage or gear orientations, etc. therein to cause selective translation. In still other embodiment, the rod 230s of the electrode 230 can translate upon any movement of the linkage 240 and/or the closure grip 220.

Energy can be applied to the electrode 230 through a variety of different mechanisms. In the illustrated embodiment, energy can be applied to the monopolar electrode 230 similar to energy applied to electrodes 219a, 219b targeting grasped tissue in the end effector 214. The actuator 226 can be depressed, actuating delivery of energy through one or more conductive members from a generator, similar to generator 52 and/or a power source similar to power source 50, to the electrode 230. The device 200 can restrict energy from being transmitted to the electrode 230 until the electrode 230 is in the extended position, at which point depression of the actuator 226 can supply energy to electrode 230 and not electrodes 219a, 219b. The device 200 can make such a determination by using a position sensor 235 that detects a proximal position of the rod 230s, determining if it is in the retracted position (such that energy is restricted to the electrode 230) or in the extended position (such that energy is restricted to the grasped tissue electrodes 219a, 219b). However, this determination can be made in a variety of other ways, such as by using one or more other rotational, magnetic, switch, pressure, etc. sensors. A user can also activate a button or switch on the proximal handle 210 to transition between a monopolar and a bipolar mode. Furthermore, in some embodiments, energy delivery can be directed to the electrodes 219a, 219b and/or the electrode 230 through a position of the actuator 226. In particular, the actuator 226 can have two ranges of motion, and it can apply energy to the electrodes 219a, 219b when moved through an initial first range, and it can apply energy to the electrode 230 when further depressed and moved through a second range. This can be preferable, for example, when limited spot treatment of tissue is desired when the electrode 230 is not in the extended position but instead has the small portion 230c exposed when it is in the retracted position. When energy is applied to the electrode 230, energy applied to a target tissue can dissipate and return through surrounding tissue and/or the device 200. In other embodiments, actuation can occur through an entirely separate actuation mechanism than the actuation mechanism for the electrodes 219a, 219b, such as a separate button, switch, etc. on the proximal handle 210. In still other embodiments, actuation mechanisms can be limited to the closure grip 220 and one actuator 224 that is used both for cutting and energy actuation.

In use, the device 200 can be used similar to device 100 when grasping tissue between the jaws 216a, 216b, transecting the grasped tissue, and applying energy thereto. The electrode 230 can initially be in the retracted position. When spot application of energy is desired, the electrode 230 can be translated from the retracted position to the extended position through pivotable movement of the closure grip 220, as discussed above. For example, jaws 216a, 216b can be in the closed position (although not grasping tissue), and the closure grip 220 can be opened to begin the process of opening the jaws 216a, 216b and extending the monopolar electrode 230. In other embodiments, the jaws 216a, 216b can be in the open position, and the closure grip 220 can be opened further to begin the process of extending the monopolar electrode 230. Once the electrode 230 is extended, energy can then be applied to target tissue by the exposed distal portion of the electrode 230. The electrode 230 can then be translated to the retracted position, again as discussed above by pivotable movement of the closure grip 220, and a user can proceed with using device 200 similar to device 100. In embodiments in which the electrode 230 can be actuated without first extending it, energy can be applied to the electrode 230 in the retracted position, and the user can spot treat limited portions of tissue as desired.

In addition to translating the monopolar electrode between a retracted and an extended position, the closure grip can be used to transition a device between a bipolar mode and a monopolar mode. FIGS. 8A-11C illustrate a surgical device 300 similar to surgical devices 100, 200 that has a monopolar electrode 330 that is translated between retracted and extended positions using a closure grip 320 on the device 300. The device 300 has a proximal handle 310, an elongate shaft 312, and an end effector 314. The shaft 312 extends distally from the proximal handle 310 and has the end effector 314 disposed on a distal end thereof, and it has at least one lumen 312a extending therethrough for carrying mechanisms for actuating the end effector 314. The end effector 314 has a first upper jaw 316a and a second lower jaw 316b that is opposed thereto. The jaws 316a, 316b can grasp tissue therebetween, transect tissue with a cutting element, and apply bipolar energy thereto through active and return electrodes. The proximal handle 310 includes a stationary grip 322 and a closure grip 320 that is pivotally movable relative to the stationary grip 322 to open and close first and second jaws 316a, 316b of the end effector 314. The cutting actuator 324 is disposed on the proximal handle 310 to cause transection of tissue grasped by the jaws 316a, 316b, energy actuator 326 is disposed on the proximal handle 310 to cause delivery of energy to the end effector 314, and rotational knob 328 is disposed between the shaft 312 and the proximal handle 310 to allow rotation of the shaft 312 and/or the end effector 314. Various gear(s), rack(s), drive screw(s), drive nut(s), motor(s), processor(s), conducting member(s), etc. can be disposed within the proximal handle 310 and/or the shaft 312 to translate actuation of the closure grip 320, the actuators 324, 326, and the rotational knob 328 into actuation of functions or rotation of the end effector 314.

Figure 11A:
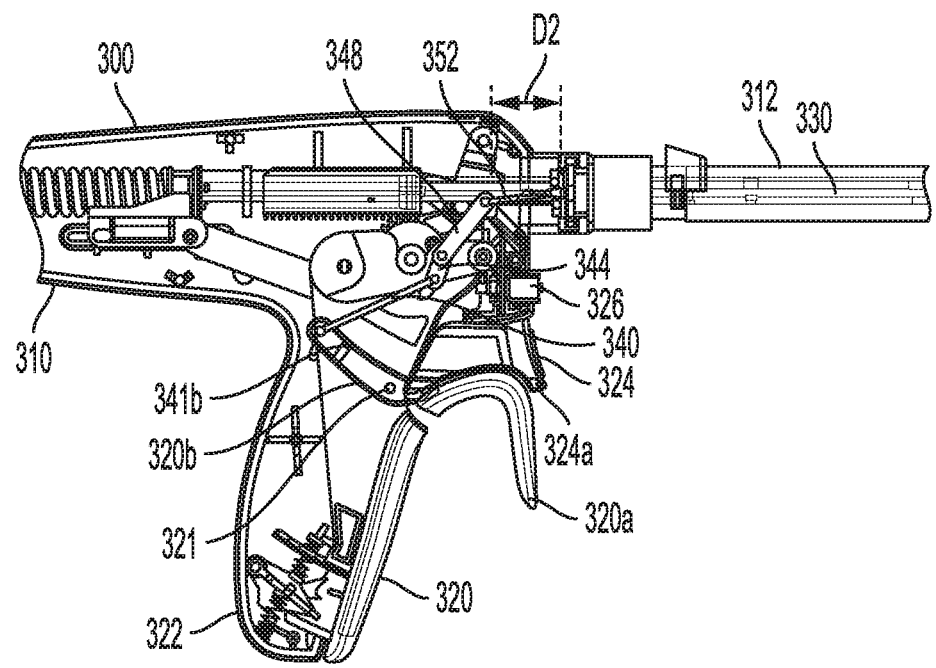
FIG. 11A is a partially-transparent side view of the surgical device of FIG. 8A.
Figure 11B:
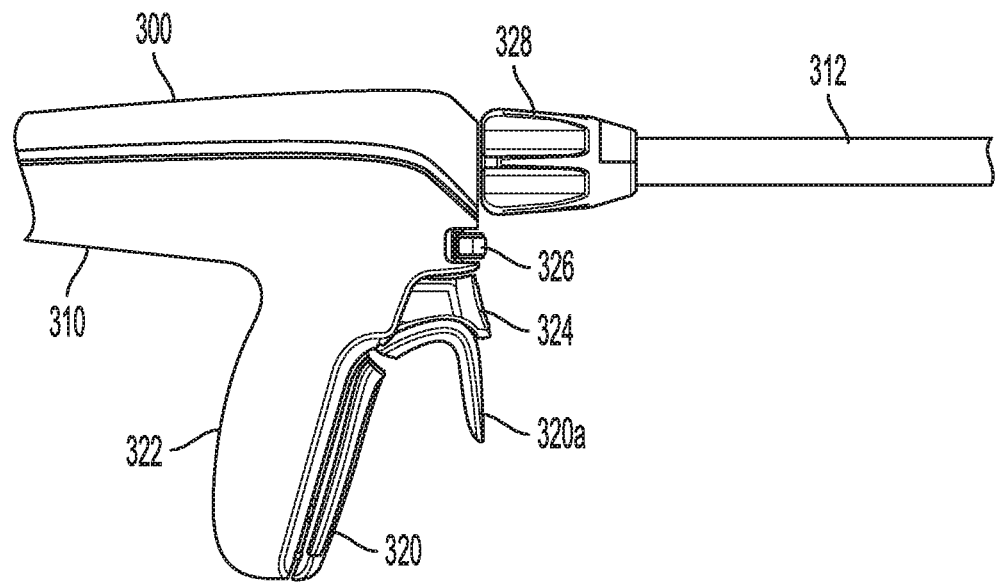
FIG. 11B is a side view of the surgical device of FIG. 8A.
Figure 11C:
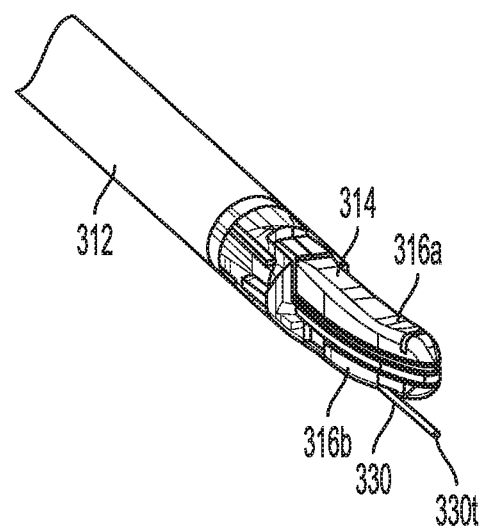
FIG. 11C is a perspective view of a distal portion of the surgical device of FIG. 8A.

A monopolar electrode 330 extends longitudinally through the end effector 314 and is longitudinally translatable distally and proximally with respect thereto. The electrode 330 is similar to electrode 230 and can translate between a retracted position in which a majority of the electrode 330 is retracted within the end effector 314, as illustrated in FIGS. 9C and 9D, and an extended position in which at least a distal tip 330t of the electrode 330 protrudes distally beyond a distal end of the end effector 314, as illustrated in FIG. 11C. Upon distal transition of the electrode 330 and actuation of energy, as discussed below, the electrode 330 can be used to spot seal, coagulate, mark, cut, etc. tissue disposed adjacent to the end effector 314. The electrode 330 has an elongate rod 330s and a distal tip 330t. The rod 330s extends proximally through a lumen 332 in the lower jaw 316b to engage with one or more conductive members in the proximal handle 310 for receiving energy therefrom. The distal tip 330t is a straight shaft, however in other embodiments the tip 330t can be an L-shaped hook similar to hook 230t. In the retracted position, the distal tip 330t can be received entirely within the end effector 314, as illustrated in FIGS. 9C and 9D, however in other embodiments the tip 330t can protrude slightly therefrom to allow minor spot treatment of tissue, similar to hook 230t. The monopolar electrode 330 can also have a nonconductive, protective sleeve therearound, similar to sleeve 234 of electrode 230, with an active distal portion of the electrode 330 extending therefrom.

Similar to electrode 230 above, electrode 330 can be extended distally from the end effector 314 through actuation of linkages engaged with the closure grip 320. Specifically, the closure grip 320 has a secondary electrode handle 320a that can move independent of the closure grip 320. The secondary electrode handle 320a is pivotally connected to the closure grip 320 such that upward distal pivotable movement of the electrode handle 320a relative to the closure grip 320 causes distal translation of the electrode 330 and transitions the device 300 into a monopolar mode. In such a mode, the cutting actuator 324 is obstructed from activating a cutting element, and the energy actuator 326 activates the monopolar electrode 330 rather than any bipolar electrodes in the end effector 314. The device 300 can operate as a bipolar electrode device when the monopolar electrode 330 is in the retracted position, such as when the secondary electrode handle 320a is positioned in a downward proximal position adjacent to the closure grip 320.

The electrode handle 320a can thus pivot distally upward relative to the closure grip 320 at pivot point 21 upon application of distal force thereto, causing the electrode 330 to translate from the retracted position to the extended position through a series of linkages and engagement in the proximal handle 310. The electrode handle 320a has a proximal bar 320b extending proximally therefrom into the proximal handle 310. A first linkage 340 is pivotally connected to a proximal end of the proximal bar at pivot point 342, and it in turn connects to a middle portion of a switch linkage 344 at pivot point 346. The switch linkage 344 has a distal end that engages a switch 326a on the energy actuator 326 and a proximal end that couples to a distal end of a second linkage 348 at pivot point 350. The second linkage 348 extends toward a proximal end of the rod 330s of the electrode, and a proximal end of the second linkage 348 couples to a proximal end of a slide 352 at a rotational point 354. Distal translation of the slide 352 distally translates the rod 330s of the electrode 330, resulting in the electrode 330 moving from the retracted position to the extended position. Proximal translation of the slide 352 causes corresponding proximal translation of the electrode 330 from the extended position to the retracted position.

Figure 8A:
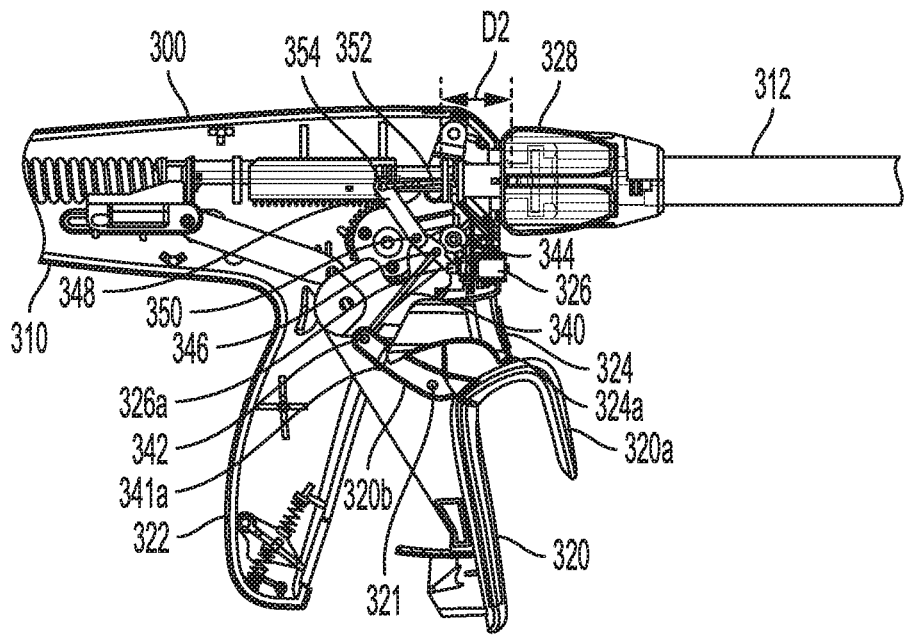
FIG. 8A is a partially-transparent side view of another embodiment of a surgical device.

The interconnected movement of the linkages can thus cause transition of the device 300 from the bipolar mode to the monopolar mode, as described herein. FIG. 8A illustrates the linkages when the closure and stationary grips 320, 322 are in the open position. In such a position, a blocking protrusion 324a of the cutting trigger 324 can rest in obstructing engagement with the secondary electrode handle 320a to prevent any upward distal force from being applied thereto. This obstruction prevents extension of the electrode 330 when the jaws 316a, 316b are in the open position. A protuberance on the proximal bar 320b sits into a first detent 341a on the closure grip 320 that helps to keep the electrode handle 320a in a stationary position relative to the closure grip 320 and indicates a retracted position of the electrode 320. The switch linkage 344 engages the switch 326a on the energy actuator 326, keeping energy application in a bipolar mode that applies energy to the gripping electrodes in the end effector 314 upon depression of the energy actuator 326. Energy is thus not applied to the monopolar electrode 330 even upon actuation of the energy actuator 326.

Figure 9A:
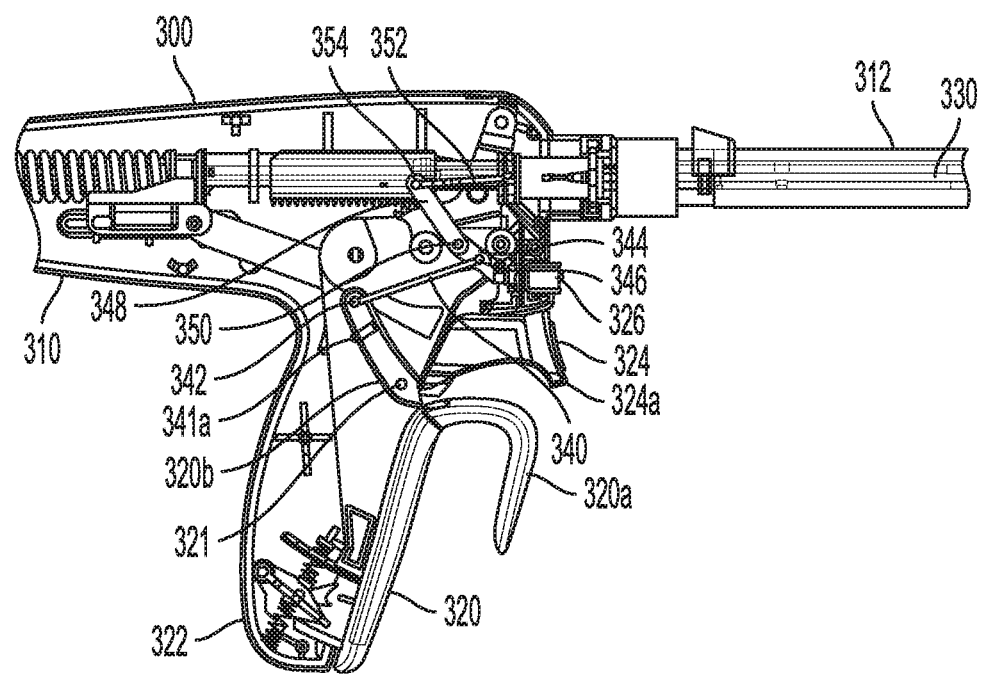
FIG. 9A is a partially-transparent side view of the surgical device of FIG. 8A.
Figure 9B:
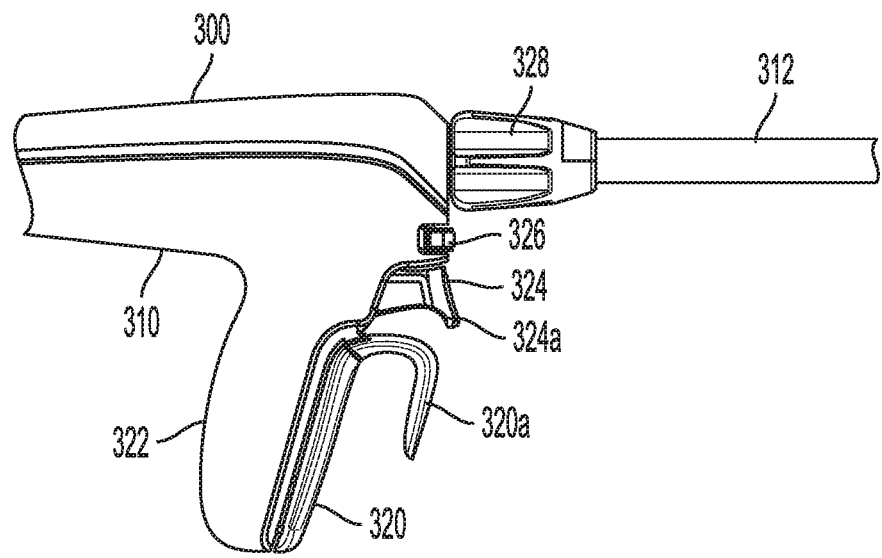
FIG. 9B is a side view of the surgical device of FIG. 8A.
Figure 9C:
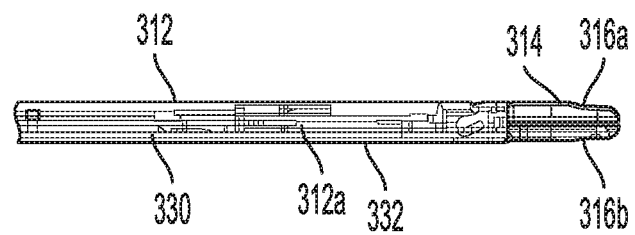
FIG. 9C is a partially-transparent side view of a distal portion of the surgical device of FIG. 8A.
Figure 9D:
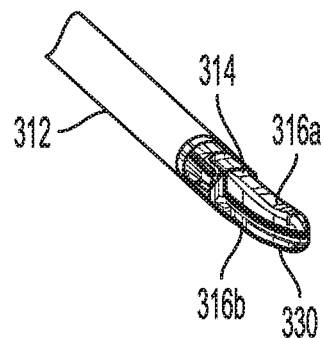
FIG. 9D is a perspective view of the distal portion of the surgical device of FIG. 9C.

When the closure grip 320 is pivotally moved to the closed position against the stationary grips 322, as illustrated in FIG. 9A, the blocking protrusion 324a is no longer in obstructive engagement with the electrode handle 320a. However, the electrode handle 320a remains in position relative to the closure grip 320, and the electrode 330 remains in the retracted position, as illustrated in FIGS. 9C and 9D. The switch linkage 344 remains in engagement with the switch 326a on the energy actuator 326, keeping energy application in a bipolar mode.

Figure 10:
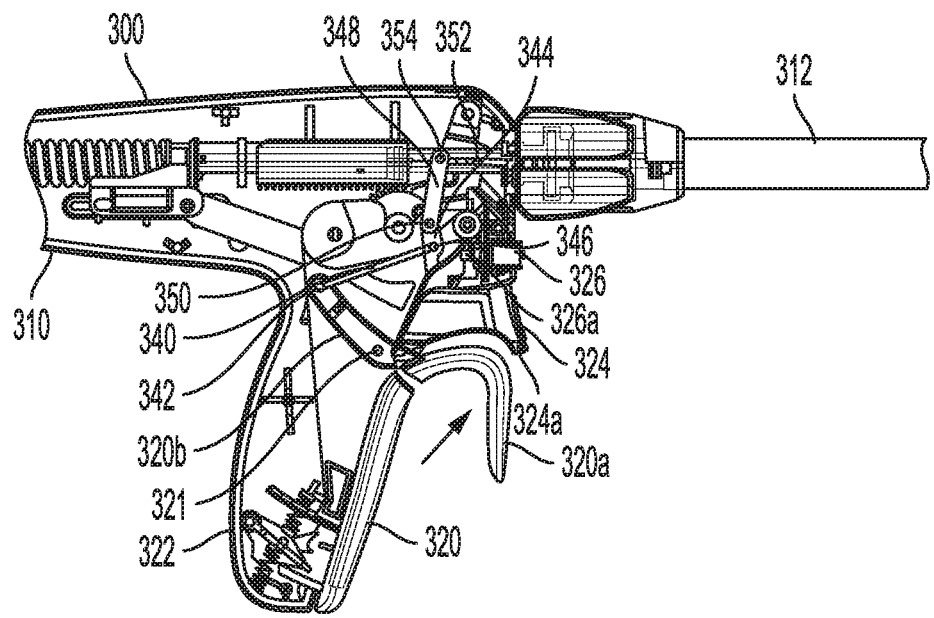
FIG. 10 is a partially-transparent side view of the surgical device of FIG. 8A.

As upward distal force is applied to the electrode handle 320a, as illustrated by an arrow in FIG. 10, the electrode handle 320a has clearance from the blocking protrusion 324a of the cutting actuator 324 to pivot distally upward relative to the closure grip 320. Additionally, the cutting actuator 324 has a semi-circular opening or cavity along a surface facing the electrode handle 320a to ensure clearance into which the electrode handle 320a can begin to pivot. As the electrode handle 320a pivots relative to the closure grip 320, the proximal bar 320b moves proximally, causing the first linkage 340 to move proximally and the switch linkage 344 to be pulled proximally out of engagement with the switch 326a on the energy actuator 326. The device 300 switches into monopolar mode with the change at the switch 326a, thus applying energy to the monopolar electrode 330 upon depression of the energy actuator 326 rather than any gripping electrodes in the end effector 314. Movement of the switch linkage 344 causes the second linkage 348 to pivot distally, forcing the slide 352 distally to translate the rod 330s of the electrode 330 distally as well. As the electrode handle 320a is fully pivoted distally upward, as illustrated in FIG. 11A, the protuberance on the proximal bar 320b engages a second detent 341b on the closure grip 320 and indicates an extended position of the electrode 320. This engagement helps to keep the electrode handle 320a in a stationary position relative to the closure grip 320 in the extended position. It also provides the user a tactile feel for when full extension of the electrode 330 is achieved. Furthermore, the electrode handle 320a pivots fully into the semi-circular opening or cavity on the cutting actuator 324 facing the electrode handle 320a. This engagement can act to lock out or obstruct proximal depression of the cutting actuator 324 because any proximal movement of the cutting actuator 324 is impeded by the electrode handle 320a. This engagement also thus subsequently prevents actuation of the cutting element in the end effector 314 when the device 300 is in monopolar mode. Movement of linkages 340, 344, 348 forces the slide 352 fully distally to translate the rod 330s of the electrode 330 distally to the fully extended position, as illustrated in FIG. 11C.

Thus upward distal pivotable movement of the electrode handle 320a causes distal translation of the slide 352 and subsequent distal translation of the electrode 330 over a distance D2, as illustrated in FIGS. 8A and 11A. It also transitions the device 300 into a monopolar mode such that the actuator 326 controls the monopolar electrode 330 and the actuator 324 cannot be actuated. Linkage movement can be correspondingly reversed to transition the device 300 into a bipolar mode by applying downward proximal force on the electrode handle 320a. Such force causes the electrode handle 320a to pivotally move out of obstructive engagement with the cutting actuator 324, corresponding proximal translation of the electrode 330 to the retracted position, and reengagement of the switch 326a with the switch linkage 344 to enter bipolar mode in which depressing the energy actuator 326 causes energy to be supplied to bipolar electrodes in the end effector 314.

Figure 8B:
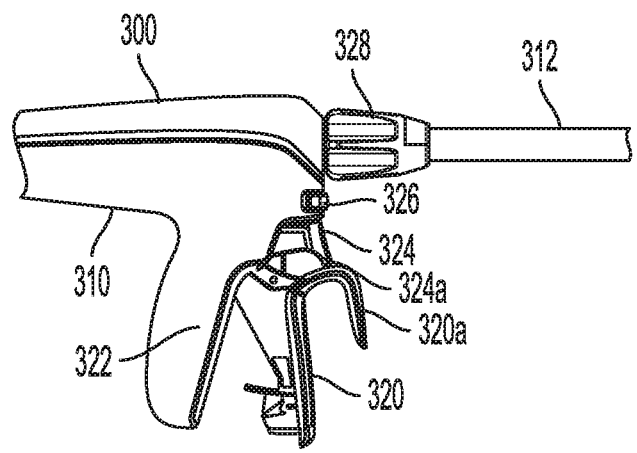
FIG. 8B is a side view of the surgical device of FIG. 8A.

In use, the device 300 can be used similar to devices 100, 200 when grasping tissue between the jaws 316a, 316b, transecting the grasped tissue, and applying energy thereto in the bipolar mode. As illustrated in FIGS. 8A and 8B, the closure grip 322 can be in an open or spaced position relative to the stationary grip 322 in which the jaws 316a, 316b are in an open position to receive tissue therebetween. Upon pivotable movement of the closure grip 320 toward the stationary grip 322, as illustrated in FIGS. 9A and 9B, the jaws 316a, 316b move to a closed or grasping position in which tissue can be grasped therebetween. In such a position, any grasped tissue can be transected upon depression of the cutting actuator 324 and/or can be sealed upon depression of the energy actuator 326. In both the open position and the initial closed position, the electrode 330 is in a retracted position, as illustrated in FIGS. 9C and 9D. When spot application of energy is desired, the electrode 330 can be translated from the retracted position to the extended position, as discussed above. For example, the jaws 316a, 316b can be moved to the closed position while not grasping tissue therebetween by pivotally moving the closure grip 320 toward the stationary grip 322. Upon full closure, the electrode handle 320a can be pivoted distally upward relative to the closure grip 320, causing the electrode 330 to extend distally into the extended position while also switching the device 300 to the monopolar mode. As such, the energy actuator 326 can be switched to activating the electrode 330, and the cutting actuator 324 can be blocked or obstructed from actuation by the electrode handle 320a. A user can proceed with using the device 300 to apply energy to target tissue at selected spots through the monopolar electrode 330. The electrode handle 320a can subsequently be moved proximally downward, and the electrode 330 can be retracted while the device 300 reenters bipolar mode.

In some embodiments, pivotable motion of the closure grip can be disconnected from translation of the monopolar electrode when using the surgical device in a bipolar mode. FIGS. 12A-13B illustrate another embodiment of a surgical device 400 similar to surgical devices 100, 200, 300 that has a monopolar electrode 430 that is translated between a retracted and extended position due to pivotable movement of a closure grip 420. The device 400 has a proximal handle 410, an elongate shaft 412, and an end effector 414. The shaft 412 extends distally from the proximal handle 410 and has the end effector 414 disposed on a distal end thereof. The shaft 412e has at least one lumen extending therethrough for carrying mechanisms for actuating the end effector 414. The end effector 414 has a first upper jaw 416a and a second lower jaw 416b that is opposed thereto. The jaws 416a, 416b can grasp tissue therebetween, transect tissue with a cutting element, and apply bipolar energy thereto through active and return electrodes therein. The proximal handle 410 includes a stationary grip 422 and the closure grip 420 that is pivotally movable relative to the stationary grip 422 to open and close the first and second jaws 416a, 416b. A cutting actuator 424 is disposed on the proximal handle 410 to cause transection of tissue grasped by the jaws 416a, 416b, an energy actuator 426 is disposed on the proximal handle 410 to cause delivery of energy to bipolar electrodes in the end effector 414, and a rotational knob 428 is disposed between the shaft 412 and the proximal handle 410 to allow rotation of the shaft 412 and/or the end effector 414. Various gear(s), rack(s), drive screw(s), drive nut(s), motor(s), processor(s), conducting member(s), etc. can be disposed within the proximal handle 410 and the shaft 412 to translate actuation of the closure grip 420, the actuators 424, 426, and the rotational knob 428 into actuation of functions or rotation of the end effector 414.

Figure 12A:
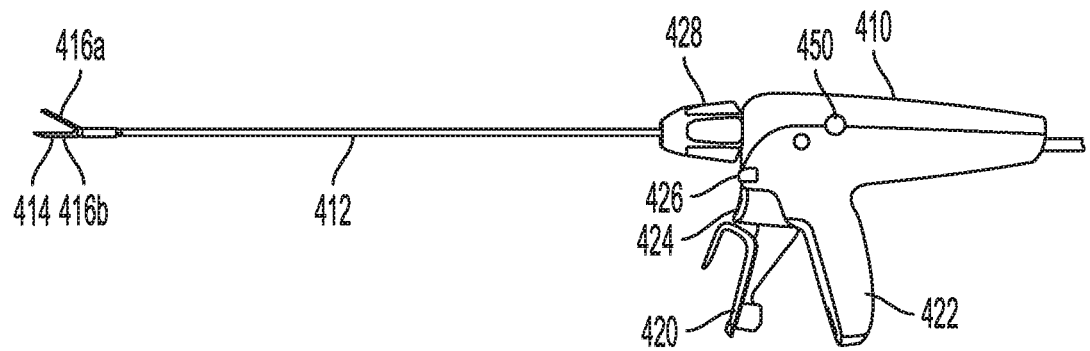
FIG. 12A is a side view of another embodiment of a surgical device.
Figure 12B:
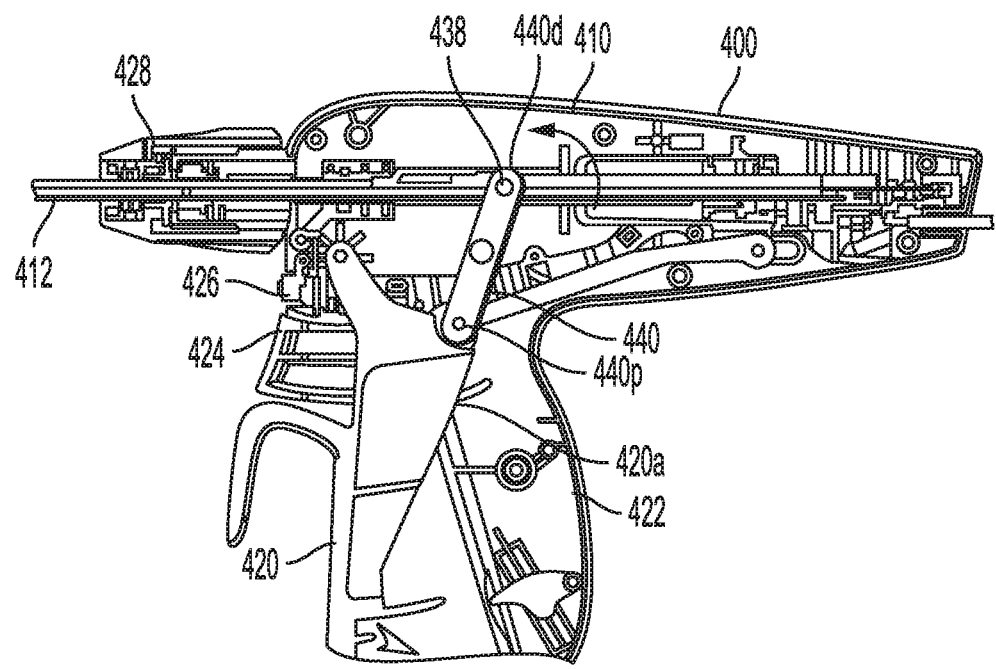
FIG. 12B is a partial cross-sectional side view of the surgical device of FIG. 12A.
Figure 12C:
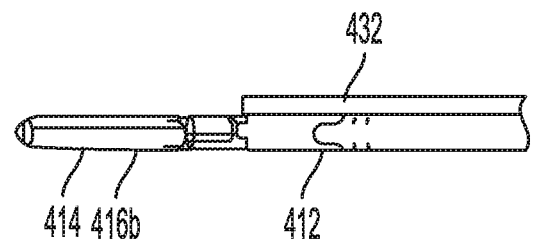
FIG. 12C is a side view of a distal portion of the surgical device of FIG. 12A.
Figure 13A:
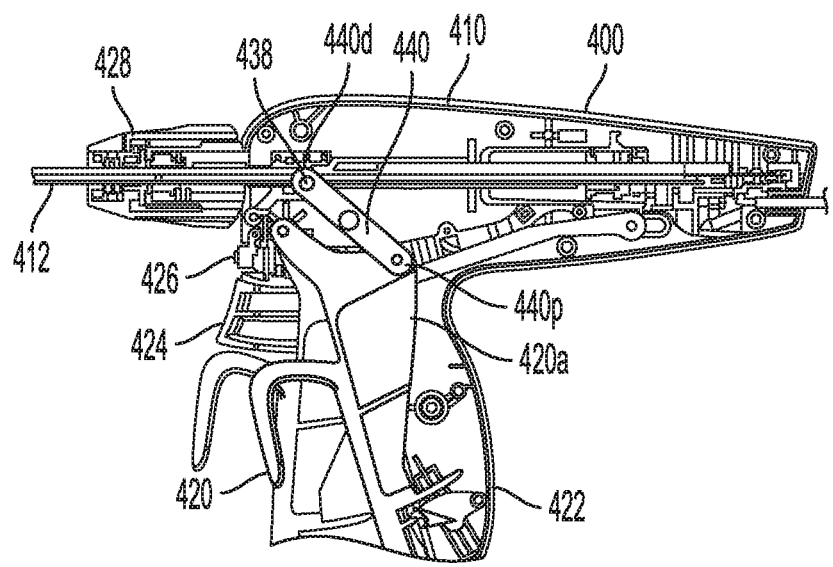
FIG. 13A is a partially-transparent side view of the surgical device of FIG. 12A.
Figure 13B:
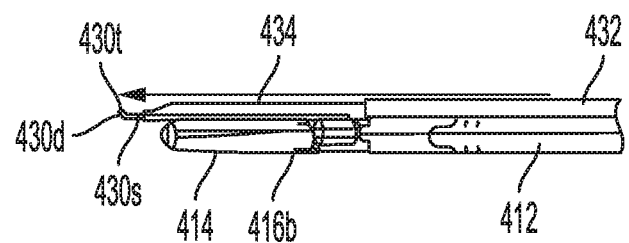
FIG. 13B is a side view of a distal portion of the surgical device of FIG. 12A.

A monopolar electrode 430 extends longitudinally along the end effector 414 and is longitudinally translatable distally and proximally with respect thereto. The electrode 430 is similar to electrodes 230, 330 and can translate between a retracted position in which a majority of the electrode 430 is retracted within the end effector 414, as illustrated in FIG. 12C, and an extended position in which at least a distal end 430d of the electrode 430 protrudes distally beyond a distal end of the end effector 414, as illustrated in FIG. 13B. Upon distal transition of the electrode 430 and actuation of energy, as discussed below, the electrode 430 can be used to spot seal, coagulate, mark, cut, etc. tissue disposed adjacent to the end effector 414. The electrode 430 has an elongate rod 430s and a distal hook 430t at its distal end 430d. The rod 430s extends proximally through the lumen 432 to engage with one or more conductive members in the proximal handle 410 for receiving energy therefrom. The distal hook 430t is an L-shaped hook similar to hook 230t. In the retracted position, the distal tip 430t can be received entirely into the end effector 414, as illustrated in FIG. 12C, however in other embodiments the tip 430t can protrude slightly therefrom to allow minor spot treatment of tissue, similar to hook 230t. The monopolar electrode 430 can also have a nonconductive, protective sleeve 434 therearound, similar to sleeve 234 of electrode 230, with an active distal portion of the electrode 430 extending therefrom.

Similar to devices 200, 300, pivotable movement of the closure grip 420 is translated into proximal and distal movement of the electrode 430 through one or more linkages or camming mechanisms in the proximal handle 410. However, the electrode 430 can be disengaged from the closure grip 420 such that pivotable movement of the closure grip 420 does not cause proximal and distal movement of the electrode 430 by a user, as discussed below. The closure grip 420 has an extension wing 420a that extends proximally into the proximal handle 410 and pivotally couples to a proximal end 440p of a first linkage 440. The first linkage 440 extends distally toward the shaft 412, and a distal end 440d of the first linkage 440 couples to an engagement member 448 that engages a proximal portion of the rod 430s of the electrode 430. It can thus pivot relative to the distal end 440d of the first linkage 440 and can translate proximally and distally to cause linear translation of the electrode 430. Thus, in a retracted position as illustrated in FIG. 12B, the distal end 440d of the first linkage 440 and the engagement member 448 are positioned proximal to the shaft 412 in the proximal handle 410. The electrode 430 is in the corresponding retracted position, as illustrated in FIG. 12C. Upon closure of the closure grip 420, as illustrated in FIG. 13A, the proximal end 440p of the linkage 440 is moved upwards proximally, forcing the distal end 440d of the first linkage 440 and the engagement member 448 to be translated distally toward the shaft 412 in the proximal handle 410, as indicated by the arrow in FIG. 12B and distal placement of the distal end 440d of the first linkage 440 and the engagement member 448 in FIG. 13A. This distal movement causes corresponding distal translation of the electrode 430 from the retracted position to the extended position, as illustrated by an arrow in FIG. 13B.

However, as noted above, engagement between movement of the closure grip 420 and translation of the electrode 430 can be selectively disconnected by a user when desired, such as when using the device 400 as a bipolar device without need for spot tissue treatment. Two opposed buttons or toggles 450 can be positioned on opposite sides of the proximal handle 410 and they can engage with the engagement member 438 within the proximal handle 410. Upon pressing the buttons 450, the engagement member 438 disengages from the rod 430s of the electrode 430. For example, one or more spring-biased pins can be retracted from the engagement member 438 and/or the linkage 440 upon pressing the buttons 450. After which, pivotal movement of the closure grip 420 does not affect translation of the electrode 430. The linkage 440 can continue to pivot and move in a channel in the proximal handle 410 upon movement of the closure grip 420, and/or the engagement member 438 can translate distally and proximally with movement of the linkage 440. When reengagement is desired, the closure grip 420 can return to the opened position (representing the retracted position of the electrode 430), and the buttons 450 on each side of the proximal handle 410 can be reactivated to reengage the engagement member 438 with the rod 430s of the electrode 430, for example by reinserting the pins into engagement. In some embodiments, the device 400 can be configured only to allow disconnection at select points, such as when the electrode 430 is in the retracted position. In other embodiments, the buttons 450 can retract toward an outer surface of the proximal handle 410 when in engagement to indicate engagement is in place, and can protrude from the outer surface of the proximal handle 410 when out of engagement to indicate engagement is not in place. A variety of engagement mechanisms are possible other than pins, such as clips, magnets, screws, protuberances and detents, etc. In other embodiments, pressing the buttons 450 to disengage the engagement member 438 from the electrode 430 can cause automatic retraction of the electrode 430 into the retracted position.

Upon pressing the buttons 450 to engage the rod 430s, the device 400 can enter a monopolar mode in which depression of the energy actuator 426 applies energy to the electrode 430. The cutting actuator 424 can be disengaged during monopolar mode such that the cutting element is not translated upon actuation thereof. In other embodiments, it can be left unaffected by monopolar mode such that actuation thereof causes translation of the cutting element through the end effector 414 even though no tissue is grasped therebetween. In some embodiments, the energy actuator 426 can be used for lower power treatments, such as coagulation or marking, and the cutting actuator 424 can be used to apply enough energy to the electrode 430 for it to serve as a cutting member when being passed through tissue. In such embodiments, the cutting element disposed in the end effector 414 can continue to be translated upon actuation of the cutting actuator 424. For example, actuation of the cutting actuator 424 by depressing the actuator 426 during most of the depression can cause translation of the cutting element with a final actuation mechanism being triggered at a final point of depression to cause cutting energy to be applied to the electrode 430. However, as noted above, in other embodiments, the cutting element can be disconnected from actuation upon entering monopolar mode. In still other embodiments, pressing the cut actuator can cause the device 400 to enter monopolar mode rather than pressing the buttons 450. However, a variety of different mechanisms can be used to transition between bipolar and monopolar modes, such as one or more sensors similar to sensors discussed above.

Upon pressing the buttons 450 to disengage the engagement member 438 from the electrode 430, the device 400 can enter a bipolar mode in which the cutting actuator 424 triggers transection of tissue grasped by the end effector 414 and the energy actuator 426 triggers sealing of the grasped tissue, as discussed above.

In use, the device 400 can be used similar to devices 100, 200, 300 when grasping tissue between the jaws 416a, 416b, transecting the grasped tissue, and applying energy thereto. The electrode 430 can initially be in the retracted position and the engagement member 438 can be disengaged from the electrode 430 such that the device 400 is in the bipolar mode. When spot application of energy is desired, the closure grip 420 can be moved from the closed position to the open position, and the buttons 450 can be actuated to cause the engagement member 438 to engage the rod 430s of the electrode 430 and the device 400 to enter monopolar mode. Upon closure of the closure grip 420, the electrode 430 can thus be translated from the retracted position to the extended position, as discussed above. Cutting energy and/or coagulation energy can be applied to the electrode 430, as discussed above, to treat target tissue adjacent to the end effector 414. When spot treatment is completed, the closure grip 420 can be moved to the open position, the buttons 450 can be pressed to disengage the engagement member 438, and the device 400 can be operated in bipolar mode once more.

All of the devices disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It is preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

One skilled in the art will appreciate further features and advantages of the described devices and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical device, comprising:
a handle having an elongate shaft extending distally therefrom;
an end effector operatively connected to a distal end of the elongate shaft, the end effector having first and second jaws movable between an open position in which the first and second jaws are spaced apart from one another and a closed position in which the first and second jaws cooperate to grasp tissue therebetween, the first and second jaws being configured to conduct bipolar energy through tissue grasped therebetween;
a conductive member extending longitudinally through the first jaw, the conductive member having a retracted position in which the conductive member is substantially disposed within the first jaw, and an extended position in which the conductive member extends at least partially distally beyond a distal end of the first jaw, the conductive member being configured to conduct monopolar energy through tissue adjacent thereto; and
a trigger coupled to the handle and movable between an open position and a closed position, the trigger being pivotally movable through a first range of motion between the open position toward the closed position to cause the opposed jaws of the end effector to move from the open position to the closed position while the conductive member remains in the retracted position, and the trigger being pivotally movable through a second range of motion during which the jaws remain in the closed position and the conductive member moves from the retracted position to the extended position, wherein the trigger moving through the second range of motion is configured to move the conductive member into the extended position to extend at least partially distally beyond the distal end of the first jaw,
wherein the conductive member is configured to conduct the monopolar energy through the tissue adjacent thereto, in a monopolar energy delivery mode, in both the retracted position and the extended position.

2. The surgical device of claim 1, wherein the conductive member has a hook on a distal end thereof.

3. The surgical device of claim 2, wherein the hook is positioned distal of a distal end of the first jaw and is oriented away from the second jaw.

4. The surgical device of claim 1, wherein the first and second jaws are configured to transect the tissue grasped therebetween.

5. The surgical device of claim 1, further comprising a generator in the handle to supply the bipolar energy to the first and second jaws and the monopolar energy to the conductive member.

6. The surgical device of claim 1, further comprising an external plug extending proximally from the handle to supply the bipolar energy to the first and second jaws and the monopolar energy to the conductive member.

7. The surgical device of claim 1, further comprising a cutting assembly being configured to extend through the jaws to transect the tissue grasped therebetween upon actuation in the closed position, and the handle is configured to prevent actuation of the cutting member when the trigger is in the second range of motion.

8. The surgical device of claim 1, wherein the end effector is configured to deliver the bipolar energy only in the bipolar mode when the conductive member is in the retracted position.

9. A surgical device, comprising:
a handle having an elongate shaft extending distally therefrom;
an end effector operatively connected to a distal end of the elongate shaft, the end effector having first and second jaws configured to grasp tissue therebetween and to conduct bipolar energy through the grasped tissue therebetween;
a closure grip extending from the handle and being pivotable relative to the handle to open and close the first and second jaws,
a secondary electrode handle coupled to the closure grip and configured to move independent of the closure grip;
a conductive member selectively extendable distally from the end effector and configured to conduct monopolar energy to tissue adjacent to the end effector;
wherein the surgical device is configured to deliver the bipolar energy through the first and second jaws and through the grasped tissue therebetween only in a bipolar mode and the conductive member is retracted proximally in the end effector, and a monopolar mode in which the conductive member is extended distally from the end effector and the surgical device is configured to deliver the monopolar energy when the conductive member is extended distally, the surgical device transitioning between the bipolar mode and the monopolar mode in response to pivotable movement of the secondary electrode handle, and
wherein the conductive member is configured to deliver the monopolar energy to the tissue when the conductive member is retracted proximally in the end effector.

10. The surgical device of claim 9, wherein only the monopolar energy can be conducted through the conductive member in the monopolar mode.

11. The surgical device of claim 9, wherein the conductive member has a hook on a distal end thereof.

12. The surgical device of claim 9, wherein the hook is positioned distal of a distal end of the first jaw and is oriented away from the second jaw in the monopolar mode.

13. The surgical device of claim 9, wherein the first and second jaws are configured to transect the tissue grasped therebetween.

14. A surgical method, comprising:
actuating a trigger assembly on a surgical device to pivotally move about a first range of motion to cause opposed first and second jaws of an end effector on the surgical device to move from an open position to a closed position and grasp tissue therebetween;
actuating an energy assembly to deliver bipolar energy only in a bipolar mode to the first and second jaws to seal the tissue grasped therein;
actuating the trigger assembly to pivotally move about a second range of motion during which the first and second jaws remain in the closed position and a conductive member in the end effector is translated to protrude distally beyond the end effector; and
actuating the energy assembly to deliver monopolar energy to the conductive member to treat tissue located adjacent thereto, wherein delivery of the bipolar energy in the bipolar mode to the first and second jaws is prevented by the trigger assembly when the conductive member protrudes distally beyond the end effector, and wherein the conductive member is configured to deliver the monopolar energy to the tissue when the conductive member is retracted proximally.

15. The surgical method of claim 14, further comprising, after actuating the energy assembly, actuating the trigger assembly to pivotally move about the second range of motion such that the conductive member retracts proximally into the end effector.

16. The surgical method of claim 14, further comprising actuating a cutting assembly on the surgical device to transect the tissue grasped between the first and second jaws.

\* \* \* \* \*

UNITED STATES PATENT AND TRADEMARK OFFICE
CERTIFICATE OF CORRECTION

| | | |
|---|---|---|
| PATENT NO. | : 11,648,049 B2 | Page 1 of 1 |
| APPLICATION NO. | : 16/375534 | |
| DATED | : May 16, 2023 | |
| INVENTOR(S) | : Matthew Schneider et al. | |

It is certified that error appears in the above-identified patent and that said Letters Patent is hereby corrected as shown below:

On the Title Page

Item (72) 3rd Inventors Name:
Please replace "Richard Timm" with "Richard W. Timm"

Signed and Sealed this
Thirteenth Day of June, 2023

Katherine Kelly Vidal
*Director of the United States Patent and Trademark Office*